US010991109B2

(12) United States Patent
Michallek et al.

(10) Patent No.: US 10,991,109 B2
(45) Date of Patent: Apr. 27, 2021

(54) METHOD FOR CHARACTERIZING PERFUSION ABNORMALITIES BY MEANS OF FRACTAL ANALYSIS OF THE INTERFACE REGION

(71) Applicant: CHARITÉ— UNIVERSITÄTSMEDIZIN BERLIN, Berlin (DE)

(72) Inventors: Florian Michallek, Berlin (DE); Marc Dewey, Berlin (DE)

(*) Notice: Subject to any disclaimer, the term of this patent is extended or adjusted under 35 U.S.C. 154(b) by 0 days.

(21) Appl. No.: 15/759,586

(22) PCT Filed: Sep. 13, 2016

(86) PCT No.: PCT/EP2016/071551
§ 371 (c)(1),
(2) Date: Mar. 13, 2018

(87) PCT Pub. No.: WO2017/046082
PCT Pub. Date: Mar. 23, 2017

(65) Prior Publication Data
US 2019/0164304 A1 May 30, 2019

(30) Foreign Application Priority Data
Sep. 14, 2015 (DE) ...................... 10 2015 217 519.7

(51) Int. Cl.
*G06T 7/48* (2017.01)
*G06T 7/00* (2017.01)
(Continued)

(52) U.S. Cl.
CPC ............ *G06T 7/48* (2017.01); *A61B 5/02028* (2013.01); *A61B 5/055* (2013.01); *A61B 5/7282* (2013.01);
(Continued)

(58) Field of Classification Search
CPC ....... G06T 5/002; G06T 7/002; G06T 7/0016; G06T 7/48; G06T 11/005;
(Continued)

(56) References Cited

U.S. PATENT DOCUMENTS

2011/0190626 A1* 8/2011 Mizuno ...................... G06T 7/12
600/425
2018/0078313 A1* 3/2018 Comaniciu ............ A61B 18/02

OTHER PUBLICATIONS

Goh et al. "Assessment of the spatial pattern of colorectal tumour perfusion estimated at perfusion CT using two-dimensional fractal analysis." European radiology 19.6 (2009): 1358-1365. (Year: 2009).*
(Continued)

*Primary Examiner* — Katrina R Fujita
(74) *Attorney, Agent, or Firm* — Collard & Roe, P.C.

(57) ABSTRACT

The present invention relates to a method for characterizing perfusion abnormalities in tissue by means of fractal analysis (FA) of at least one part of an interface region between adequately and abnormally perfused tissue comprising the steps of providing an imaging dataset of perfusion imaging; wherein said imaging dataset visualizes the at least one part of the interface region; optional pre-processing of said imaging dataset; applying fractal analysis to the imaging dataset; wherein said fractal analysis provides at least one fractal parameter, preferably fractal dimension (FD), of the at least one part of the interface region.

17 Claims, 7 Drawing Sheets

Figure 1:
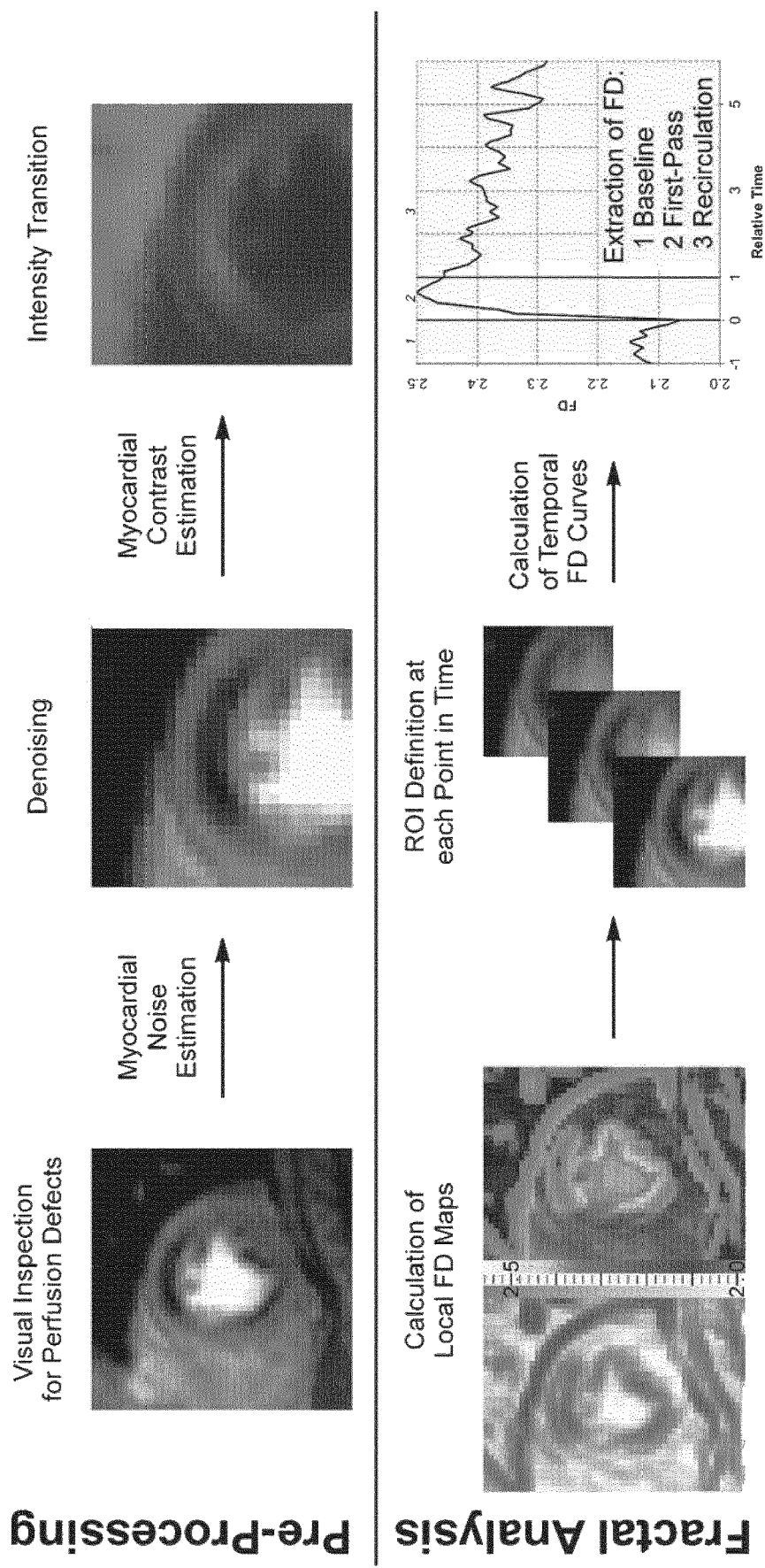

(51) Int. Cl.
| | |
|---|---|
| A61B 5/02 | (2006.01) |
| A61B 5/055 | (2006.01) |
| A61B 5/00 | (2006.01) |
| A61B 6/03 | (2006.01) |
| A61B 6/00 | (2006.01) |
| G06K 9/62 | (2006.01) |
| G06T 5/00 | (2006.01) |
| G06T 11/00 | (2006.01) |

(52) U.S. Cl.
CPC ............. *A61B 6/032* (2013.01); *A61B 6/504* (2013.01); *A61B 6/5217* (2013.01); *G06K 9/6298* (2013.01); *G06T 5/002* (2013.01); *G06T 7/0016* (2013.01); *G06T 11/005* (2013.01); *G06T 2207/10016* (2013.01); *G06T 2207/10081* (2013.01); *G06T 2207/10088* (2013.01); *G06T 2207/20032* (2013.01); *G06T 2207/20076* (2013.01); *G06T 2207/30016* (2013.01); *G06T 2207/30048* (2013.01); *G06T 2207/30096* (2013.01); *G06T 2207/30104* (2013.01)

(58) Field of Classification Search
CPC . G06T 2207/10016; G06T 2207/10081; G06T 2207/10088; G06T 2207/20032; G06T 2207/20076; G06T 2207/30016; G06T 2207/30048; G06T 2207/30096; G06T 2207/30104; A61B 5/02028; A61B 5/055; A61B 5/7282; A61B 6/032; A61B 6/504; A61B 6/5217; G06K 9/6298
See application file for complete search history.

(56) References Cited

OTHER PUBLICATIONS

Sanghera et al. "Reproducibility of 2D and 3D fractal analysis techniques for the assessment of spatial heterogeneity of regional blood flow in rectal cancer." Radiology 263.3 (2012): 865-873. (Year: 2012).*

Moore et al. "Quantifying left ventricular trabeculae function—application of image-based fractal analysis." Physiological reports 1.4 (2013). (Year: 2013).*

International Search Report of PCT/EP2016/071551, dated Dec. 5, 2016.

Michallek et al., "Fractal analysis of the ischemic transition region in chronic ischemic heart disease using magnetic resonance imaging", Eur Radiol., DOI 10.1007/s00330-016-4492-2, Jul. 19, 2016, 10 pages.

Epstein et al., "Hemodynamic Principles in the Control of Coronary Blood Flow", Am J Cardiol. 1985; 56: 4E-10E, 7 pages.

Cannon et al., "Angina Caused by Reduced Vasodilator Reserve of the Small Coronary Arteries", J Am Coll Cardiol, 1983; 1 (6): pp. 1359-1373.

Herrmann et al., "Coronary microvascular dysfunction in the clinical setting: from mystery to reality", European Heart Journal (2012); 33, pp. 2771-2782b.

Cerqueira et al., "Standardized Myocardial Segmentation and Nomenclature for Tomographic Imaging of the Heart", A Statement for Healthcare Professionals from the Cardiac Imaging Committee of the Council on Clinical Cardiology of the American Heart Association, AHA Scientific Statement, Circulation 2002; 105, pp. 539-542.

Novianto et al., "Near optimum estimation of local fractal dimension for image segmentation", . Pattern Recognition Letters 24 (2003), pp. 365-374.

Peleg et al., "Multiple Resolution Texture Analysis and Classification", IEEE Trans Pattern Analysis and Machine Intelligence, vol. PAMI-6, No. 4, Jul. 1984, pp. 518-523.

Vavere et al., Diagnostic Performance of Combined Non-invasive Coronary Angiography and Myocardial Perfusion Imaging Using 320 Row Detector Computed Tomography: Design and Implementation of the CORE320 Multicenter, Multinational Diagnostic Study, J Cardiovasc Comput Tomogr., 2011; 5(6), pp. 1-21.

Charalampidis et al., "Anatomy and Flow in Normal and Ischemic Microvasculature Based on a Novel Temporal Fractal Dimension Analysis Algorithm Using Contrast Enhanced Ultrasound", IEEE Transactions on Medical Imaging, IEEE Service Center, vol. 25, No. 8, Aug. 2006, pp. 1079-1086.

Jerosch-Herold et al., "Time Delay for Arrival of MR Contrast Agent in Collateral-Dependent Myocardium", IEEE Trans Med Imaging. 2004; 23:881-890.

International Preliminary Report on Patentability with Written Opinion of the International Searching Authority in PCT/EP2016/071551, dated Mar. 28, 2018.

* cited by examiner

METHOD FOR CHARACTERIZING PERFUSION ABNORMALITIES BY MEANS OF FRACTAL ANALYSIS OF THE INTERFACE REGION

CROSS REFERENCE TO RELATED APPLICATIONS

This application is the National Stage of PCT/EP2016/071551 filed on Sep. 13, 2016, which claims priority under 35 U.S.C. § 119 of German Application No. 10 2015 217 519.7 filed on Sep. 14, 2015, the disclosure of which is incorporated by reference. The international application under PCT article 21(2) was published in English.

The present invention relates to a method for characterizing perfusion abnormalities in tissue by means of fractal analysis and a data processing program for carrying out the same.

DESCRIPTION

Fractal analysis (FA) is a method to study an object's geometrical complexity, or roughness. It can be applied to objects that feature self-similarity (for instance in an exact, statistical or qualitative sense) over an infinite or finite range of scales.

Perfusion is regarded as a continuously distributed physiological variable describing the dynamics of blood supply to a tissue or an organ or, respectively, an area or compounds thereof, in the following summarized and referred to as "tissue", in particular human tissue, for example the myocardium (of the human heart), brain, liver, prostate or tumors (the latter can be considered as tissue compounds).

A pathological deviation of the normal, or physiological, perfusion of specific tissue is referred to as perfusion abnormality, like for instance hypoperfusion, i.e. ischemia, or hyperperfusion, such as e.g. in hemangiomas or tumors.

It is possible to visualize perfusion by means of imaging methods, for instance computed tomography (CT) or magnetic resonance imaging (MRI). In clinical practice, imaging may be performed if tissue is suspected to be abnormally perfused, e.g. in suspected ischemia.

In the following, motivation and relevance of the present invention are illustrated using the example of chronic myocardial ischemia and using data from the study of Michallek and Dewey. Eur Radiol. 2016; DOI 10.1007/s00330-016-4492-2. However, the basic aspects generally apply independently from the studied type of tissue, perfusion abnormality or imaging modality and may be extended, e.g. according to individual pathophysiological mechanisms.

Evidence that has emerged over the last decades demonstrates that obstructive coronary artery disease (CAD), i.e. macrovascular stenosis, is merely one possible pathomechanism leading to chronic myocardial ischemia and its clinical manifestation, angina pectoris. Microvascular functionality adaptively regulates coronary resistance to maintain adequate blood flow depending on epicardial driving pressure. This intricate system can be subject to functional and morphological alterations leading to ischemia even when no appreciable epicardial stenosis is present—a phenomenon that has been termed coronary microvascular dysfunction (CMD).

The pathophysiology of myocardial ischemia can therefore be understood as a composition of different underlying pathomechanisms, each with an individual significance in a given patient.

Both CAD and CMD are considered common pathomechanisms of chronic myocardial ischemia. CMD was reported to occur with a slight predominance in women. Especially in women presence of CMD is associated with a significantly higher rate of major adverse outcomes. Therefore, individual characterization of the composition of pathomechanisms underlying myocardial ischemia plays a crucial role for clinical management.

In order to explicitly evaluate ischemia in perfusion imaging, it is possible to apply vasodilative stress, which challenges the vasodilative capacity of blood vessels, e.g. by intravenous administration of adenosine. Thus, it is possible to demask impaired vasodilator reserve, synonymous to manifest ischemia. This allows studying the spatial and temporal extent of ischemic perfusion defects.

In case of myocardial ischemia, the presently used clinical routine perfusion imaging essentially provides a trichotomous differentiation between no detectable perfusion defect, isolated vasodilator stress-induced perfusion defect and a fixed perfusion defect, i.e. a perfusion defect occurring with or without vasodilative stress. So far, no method has been developed to characterize the underlying pathomechanisms of ischemia and their interaction, i.e. the pathomechanical composition, in an individual manner.

There is still the need and desire to provide a method for analyzing perfusion abnormalities in tissues, for instance in terms of pathophysiological composition and severity of chronic ischemia in the myocardium. The method is in principle applicable to all types of perfusion abnormalities, tissues and imaging modalities.

The present method provides an approach to overcome the previous shortcomings and gaps.

Thus, a method for characterizing perfusion abnormalities in tissue by means of fractal analysis (FA) of at least one part of an interface region between adequately and abnormally perfused tissue or between perfusion differences within an abnormality is provided, which comprises the steps of
- providing an imaging dataset of perfusion imaging; wherein said imaging dataset visualizes the at least one part of the interface region;
- optionally pre-processing of said imaging dataset;
- applying fractal analysis to the imaging dataset;
- wherein said fractal analysis provides at least one fractal parameter, preferably fractal dimension (FD), of the at least one part of the interface region, and
- optionally evaluating the results of fractal analysis.

The present method is based on the following novel concept: A present perfusion abnormality (for instance but not limited to focal tissue ischemia) causes an interface region within the respective tissue, where adequately and abnormally perfused areas merge into each other. This interface region might exhibit distinct perfusion patterns that vary according to the characteristics of the perfusion abnormality, e.g. its pathomechanical composition or severity. These perfusion patterns could thus serve as an alternative target to characterize perfusion abnormalities in the individual patient. The present method provides a novel approach to analyze said perfusion patterns using fractal analysis (FA) thereby quantifying the interface region's geometrical complexity. As a result, FA can be used to characterize perfusion abnormalities on a pathophysiological basis.

It is to be understood that the present method can be applied to specific parts of the interface region, which may thus be divided into segments, for example in case of myocardial ischemia into myocardial segments. It is however also conceivable to apply the present method to the interface region as a whole.

Mechanisms of vasomotion, i.e. vascular dilation (vasodilation) and vascular constriction (vasoconstriction), which control perfusion are regulated at different vascular levels, or scales. The regulatory part of the vasculature mainly includes small intramural arteries, pre-arterioles and arterioles. A scale-specific distinctive responsiveness to physical, metabolic and neural stimuli controls hemodynamics in the subsequent vascular scales, thereby regulating perfusion in the subordinated tissue regions corresponding to the specific scale. The perfusion pattern that results from the superimposition of these various scales may exhibit self-similar scaling in a statistical sense, thus being amenable to FA.

As mentioned above, the present method comprises the following steps:
perfusion imaging (to provide a perfusion imaging dataset)
optional pre-processing (of the perfusion imaging dataset)
fractal analysis (of the optionally pre-processed perfusion imaging dataset)
optional evaluation of the results of fractal analysis (of the optionally pre-processed perfusion imaging dataset).

Perfusion imaging provides an imaging dataset that can be obtained from different imaging modalities, for instance computed tomography (CT) or magnetic resonance imaging (MRI). In an embodiment the perfusion imaging is performed using an imaging modality or method capable of recording perfusion characteristics of tissue, in particular of at least one part of the interface region. Perfusion imaging preferably visualizes the temporal dynamics of contrast between blood and tissue. Contrast can be induced for instance by using an external contrast agent (e.g. intravenously or orally administered) or by using techniques that do not depend on such external contrast agent administration (e.g. arterial spin labeling in MRI). In any case, perfusion imaging may be performed using any suited imaging modality.

In a preferred embodiment of perfusion imaging, perfusion is depicted in i ($i \geq 1$) discrete representations, or snapshots, in the perfusion imaging dataset in the form of a temporally resolved image series consisting of n successively acquired individual images. Thus, in an embodiment of the present method the perfusion imaging data are organized in way that is accessible to data processing, preferably as an imaging dataset that comprises at least one temporally resolved image series consisting of i ($i \geq 1$) successively acquired individual images An imaging dataset or any parts thereof (e.g. an image, the whole image series, any combination or sub-series of the image series or a mathematical reformation of the imaging dataset), in the following summarized and referred to as "imaging dataset", can be rendered by pixels with a pixel's intensity, i.e. the gray-level value, being determined from its respectively representing tissue volume's inherent properties, imaging-related properties or contrast dynamics-related properties.

The perfusion imaging uses an induced contrast between blood and tissue. Perfusion may be visualized in different physically or physiologically well-defined phases. Thus, in an embodiment of the present method the at least one interface region may be analyzed by fractal analysis at n($n \geq 1$) individual or separate phases of perfusion or a combination thereof.

The n($n \geq 1$) individual perfusion phases may be defined for instance according to meaningful physical or physiological criteria; wherein examples of perfusion phases include baseline phase (characterized by lack of said contrast), first-pass phase (characterized by a perfusion front that occurs from the dynamics of induced said contrast during its initial occurrence and propagation) or recirculation phase (characterized by established distribution of said contrast or little dynamics of said contrast compared to the first-pass phase).

Perfusion imaging might depict any single one of these individual phases or a combination of different phases. These phases may include:
baseline phase that includes native images, i.e. without or before induced contrast,
first-pass phase that includes images that visualize a perfusion front that occurs from the dynamics of induced contrast during its initial occurrence and propagation,
recirculation phase that includes images with established distribution of contrast (for instance by effects of systemic recirculation of external contrast agents, contrast equilibrium or steady-state within tissue or a combination of mechanisms) or images with little contrast dynamics compared to the first-pass phase.

These phases can be illustrated in the context of myocardial perfusion imaging using an external contrast agent: The baseline phase includes images before the contrast agent has reached the myocardium. The first-pass phase includes images with initial contrast-uptake of the myocardium and its propagation throughout the myocardial transmurality and ends after a majority of contrast agent has passed the left ventricle before systemic recirculation. The recirculation phase includes subsequent images with systemically distributed contrast agent recirculating through the myocardium featuring a steady-state of contrast agent deposition in and removal from the myocardium and elimination of contrast agent.

In case of the present method it would be sufficient to consider only one phase or at least two phases, for example first-pass phase and/or recirculation phase or any possible combination. It is also conceivable to consider any further phases depending on the specific application. It is also conceivable that no specifically defined phase is required for applying the present method.

However, in a preferred embodiment at least two, preferably at least three different perfusion phases are considered which may comprise a baseline phase, a first-pass phase and a recirculation phase.

A present perfusion abnormality causes an interface region between adequately and abnormally perfused areas. The present method targets this interface region to characterize said perfusion abnormality on a pathophysiological basis. Therefore the perfusion imaging comprises at least one part of said interface region.

The optional pre-processing step consists of mathematical operations that can be applied to the imaging dataset including but not limited to noise filtering, intensity transitions according to certain mathematical operations, registration algorithms, segmentation algorithms or combinations, extensions or variations thereof. The purpose of an optional pre-processing is to provide an optimal preparation of the imaging dataset according to the specific context (e.g. the specific tissue being imaged or the specific imaging modality used for perfusion imaging). A preferred embodiment of the present invention may optionally feature said pre-processing.

Fractal analysis (FA) is basically accomplished by studying an arbitrarily chosen property of an object under varying resolutions. FA may provide several parameters including the fractal dimension (FD), which reflects the studied object's geometrical complexity, or roughness.

FA may be performed on different types of objects or any parts thereof, including but not limited to textures (for instance digital images or the precedingly defined imaging dataset can be interpreted as textures), dichotomous or dichotomized (e.g. thresholded) digital images or said imaging dataset, mathematical or natural objects or digital images thereof (including depiction in said imaging dataset), graphs, curves or signals (e.g. representing experimental data, mathematical phenomena or other data including said imaging dataset).

A preferred embodiment of the present method may perform FA on a texture. An m-dimensional (m≥1) image or an image series, in particular part of said imaging dataset, can be interpreted as a texture or terrain map with each pixel's intensity being considered as the texture's height and representing an (m+1)-th dimension. When applying FA to a texture, the FD may then integrate absolute height differences and their spatial distribution, thereby quantifying the texture's complexity.

For instance, in case of textures embedded in a two-dimensional space, FD ranges from 2 to 3. As the FD approaches 2.0, complexity decreases and the more the texture resembles a "flat plane". An FD approaching 3.0 indicates increasing complexity, meaning that the texture more and more resembles a three-dimensional space-filling object.

A manifold of FA methods are available. For instance, these methods can be subdivided into global and local methods, or monofractal or multifractal methods. Global FA methods consider a given object as a whole thus yielding a global FD that is representative for the whole object. If the object is a texture or a region of interest (ROI) within the texture, every available pixel thereof is considered concurrently to obtain the global FD. Local FA methods consider a certain local adjacency of the object thus yielding a local FD representative for this adjacency. Some local FA methods allow obtaining a global FD of the whole object by averaging the local FD of the respective adjacencies. Monofractal methods consider the studied object as a single fractal with one single FD. Multifractal methods may consider the object as a composition of objects with different FD, or as an object with varying fractal behavior. Thus, multifractal methods may yield a fractal spectrum, e.g. of the FD, as fractal parameter.

Any FA method may be eligible to an embodiment of the present method, thus, it does not depend on a certain FA method.

Perfusion imaging yields an object (in particular the imaging dataset) that may be of different types (e.g. textures, graphs, signals or dichotomized images). In a preferred embodiment of the present invention, FA may be applied to this object or any part thereof. The specific method of FA may vary, among other factors, according to the type of the object.

As described, FA is at least performed for at least one part of the previously defined interface region.

In another preferred embodiment of the present invention, FA may or may not be performed discretely for at least one of the preceding defined perfusion phases.

For example FA may be performed for at least two perfusion phases, in particular first-pass and/or recirculation. It is however also preferred if fractal analysis is performed for each of the previously defined perfusion phases, i.e. baseline, first-pass and recirculation.

It is also conceivable to perform FA using the complete dataset regardless of the different perfusion phases. It is also possible to analyze singular datasets independently of the perfusion phase.

In another preferred embodiment of the present method, a region of interest (ROI) may be selected in which FA is either performed, or from which results of FA are evaluated. The ROI is chosen from said imaging dataset. For a meaningful analysis, the ROI should share common features in terms of anatomy, pathology, (patho-) physiology or the imaging method.

In a preferred embodiment of the present method, said fractal parameters are evaluated in a manner that meaningfully characterizes the perfusion abnormality, for instance but not limited to the pathophysiological composition of said perfusion abnormality or its severity. This can for instance be accomplished by discretely considering said perfusion phases as these may reflect different characteristics of the perfusion abnormality.

In the example of myocardial ischemia, a suited evaluation step of FA can be implemented as follows. An irregularly shaped ROI is placed in said imaging dataset within said interface region. Depending on the employed method of FA, at least one value of the fractal parameter, e.g. FD, is calculated by FA for at least one part of the interface region at least in two different perfusion phases, in particular at least in the first-pass phase and the recirculation phase.

An ischemic defect pathologically exhibits complexity of perfusion compensating mechanisms in said interface's texture. In conclusion from the pathophysiological considerations introduced in the following paragraph ("Pathophysiological Mechanisms Using the Example of Chronic Myocardial Ischemia"), the maximum complexity during the first-pass perfusion phase ($FD_{first-pass}$) is assumed to reveal the predominant pathomechanism underlying ischemia with high, intermediate, and low $FD_{first-pass}$ reflecting CAD, CMD or collateralized CAD, and a physiological perfusion front, respectively.

With increasing delay from contrast induction, replenishment of a perfusion defect with contrast is more markedly impaired in more severely ischemic myocardium as compared to less sever defects. Consequently, complexity during recirculation phases is pathologically elevated with the extent depending on how severely perfusion is compromised. Therefore, mean complexity during recirculation ($FD_{recirculation}$) is assumed to reflect the severity of ischemia, defined either according to the restriction of absolute coronary flow reserve of that region, i.e. functional impairment, or according to the extent and relevance of the underlying structural alterations.

Figure 2:
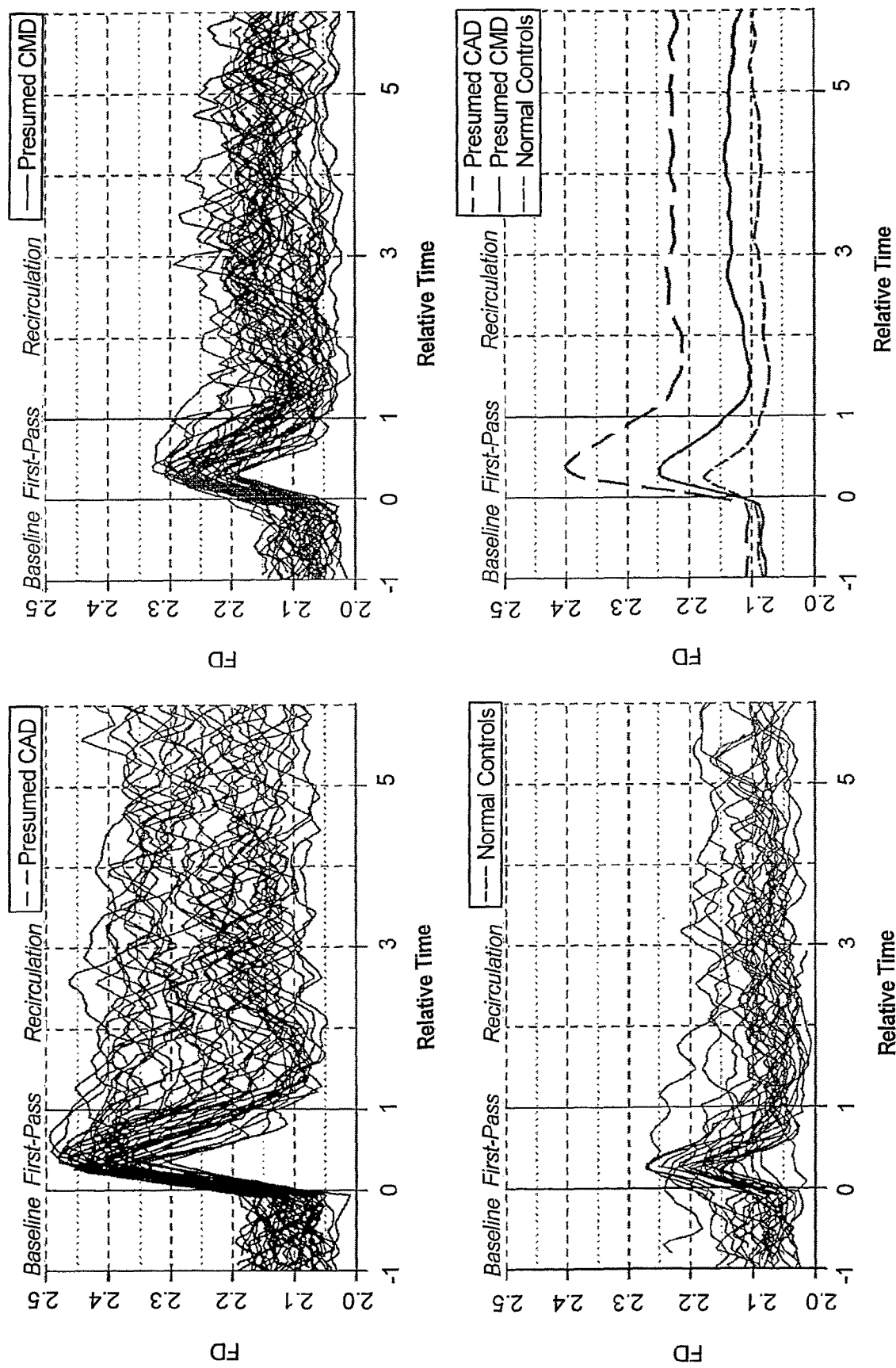
Figure 3:
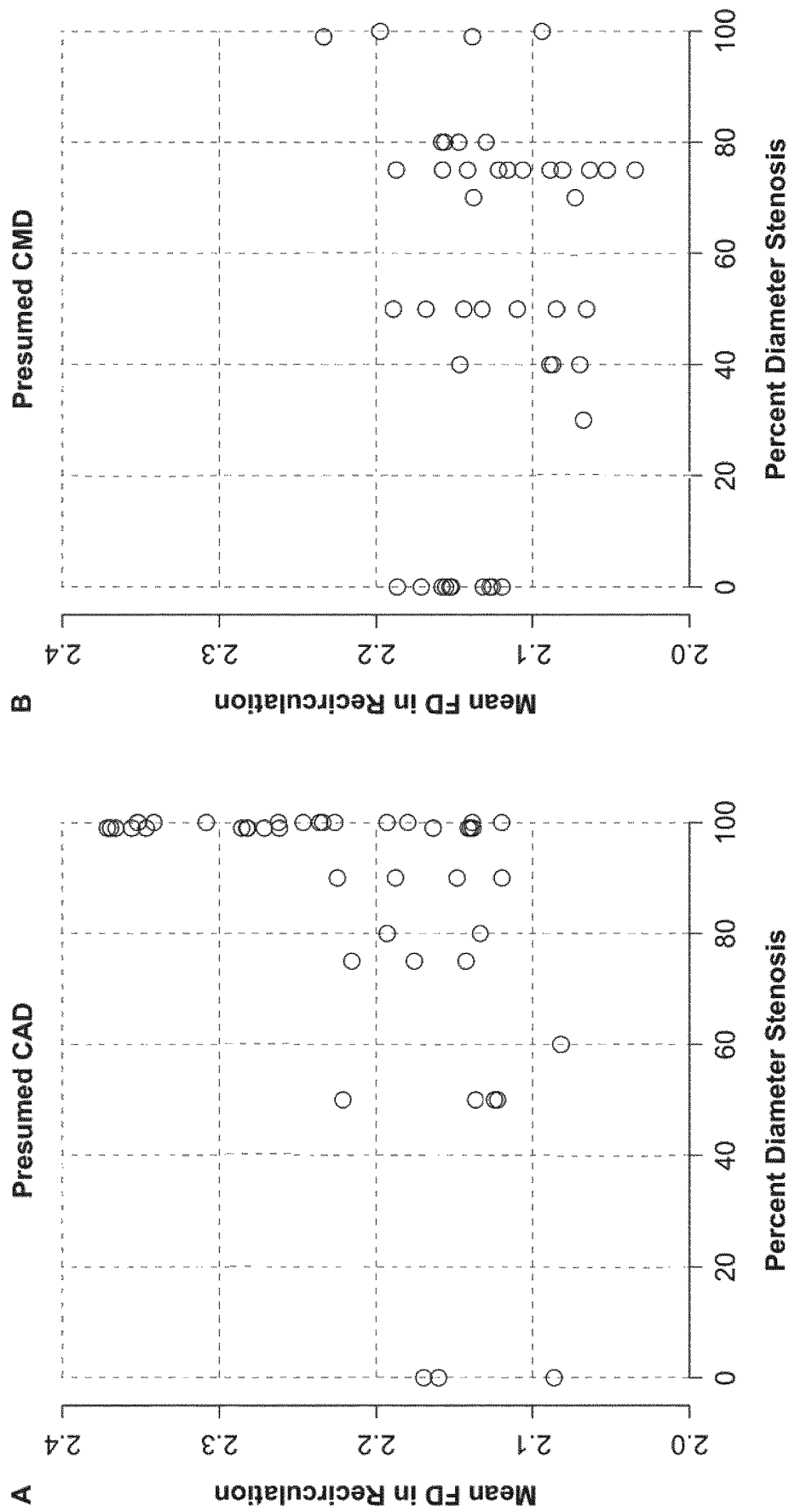
Figure 4:
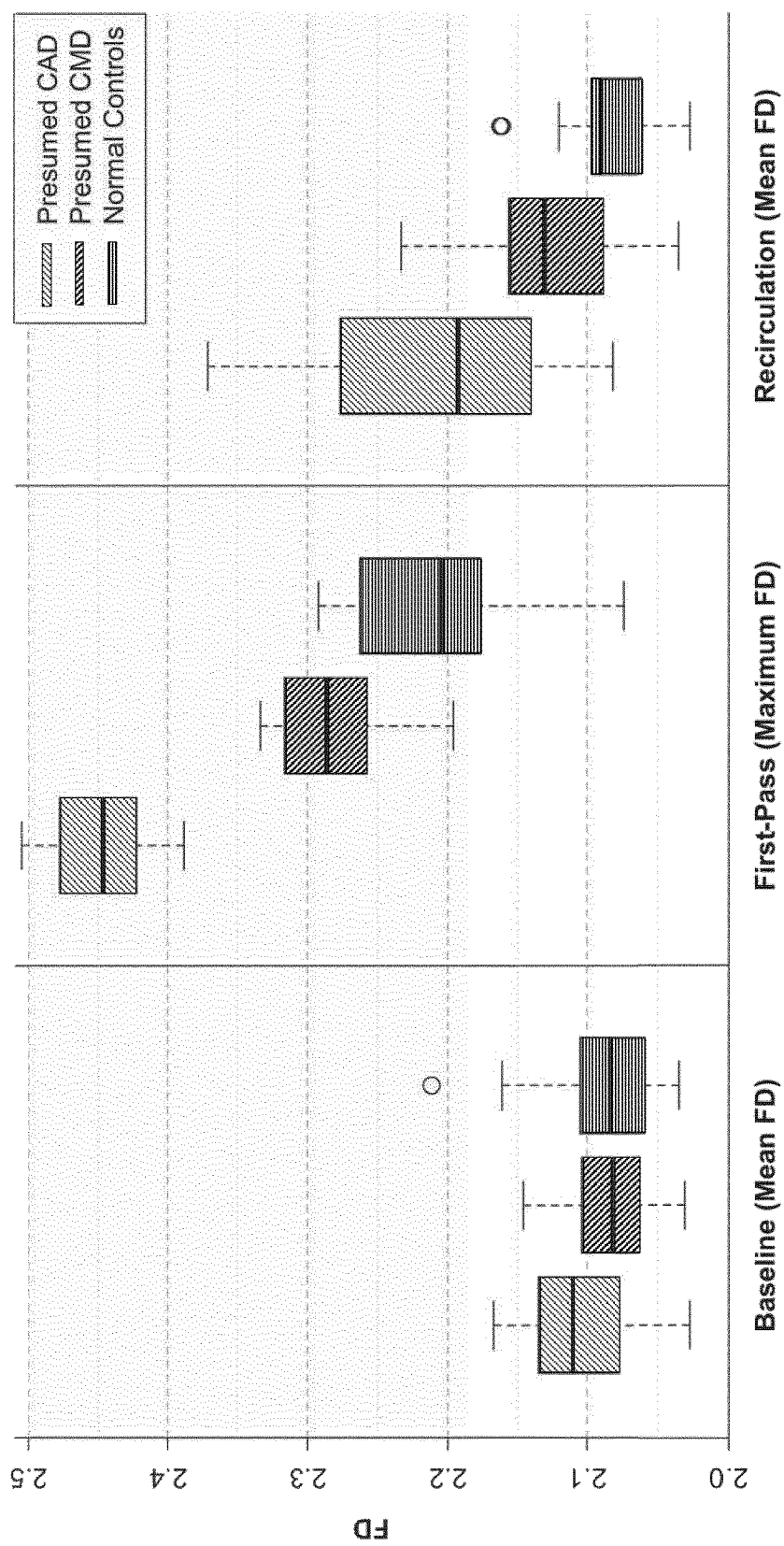
Figure 5:
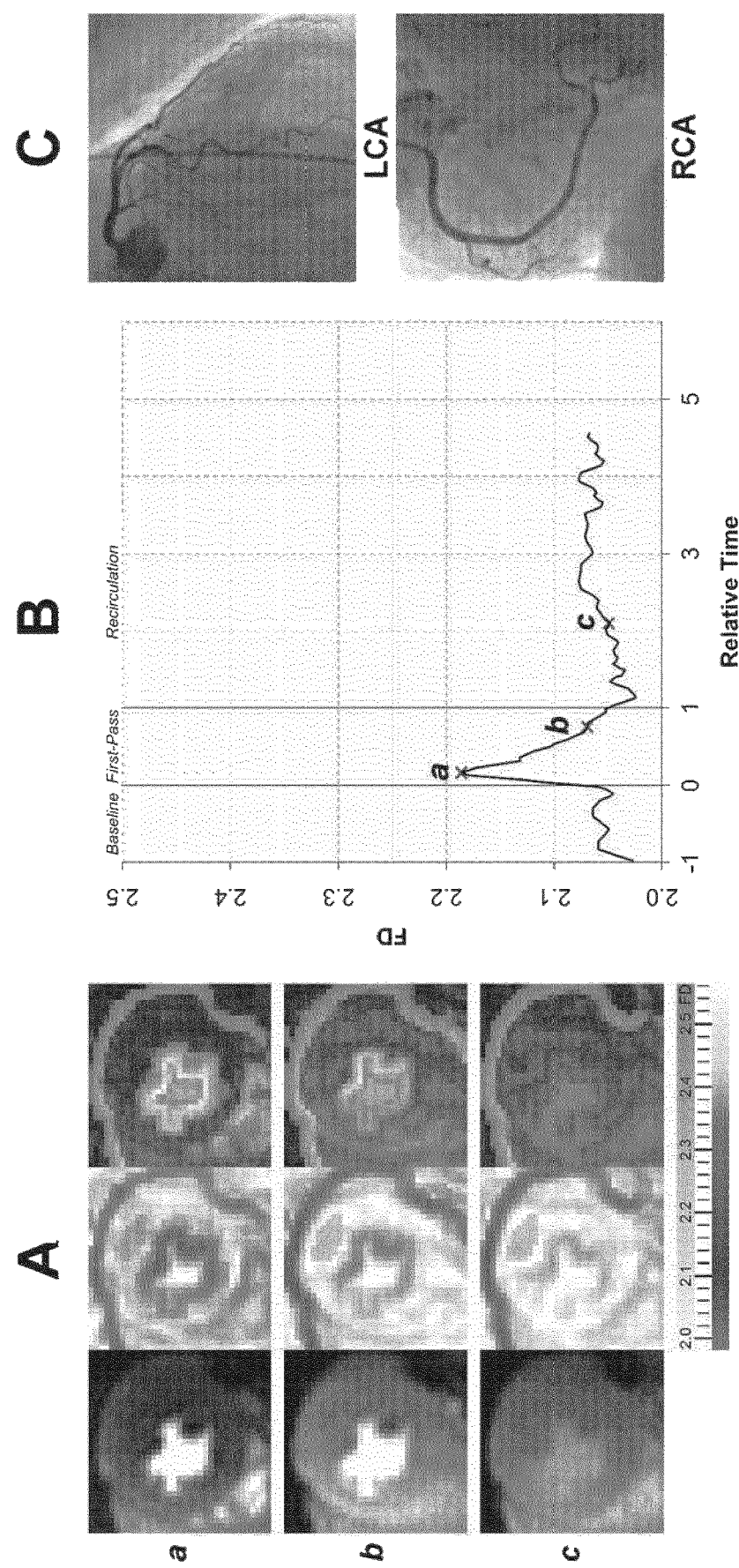
Figure 6:
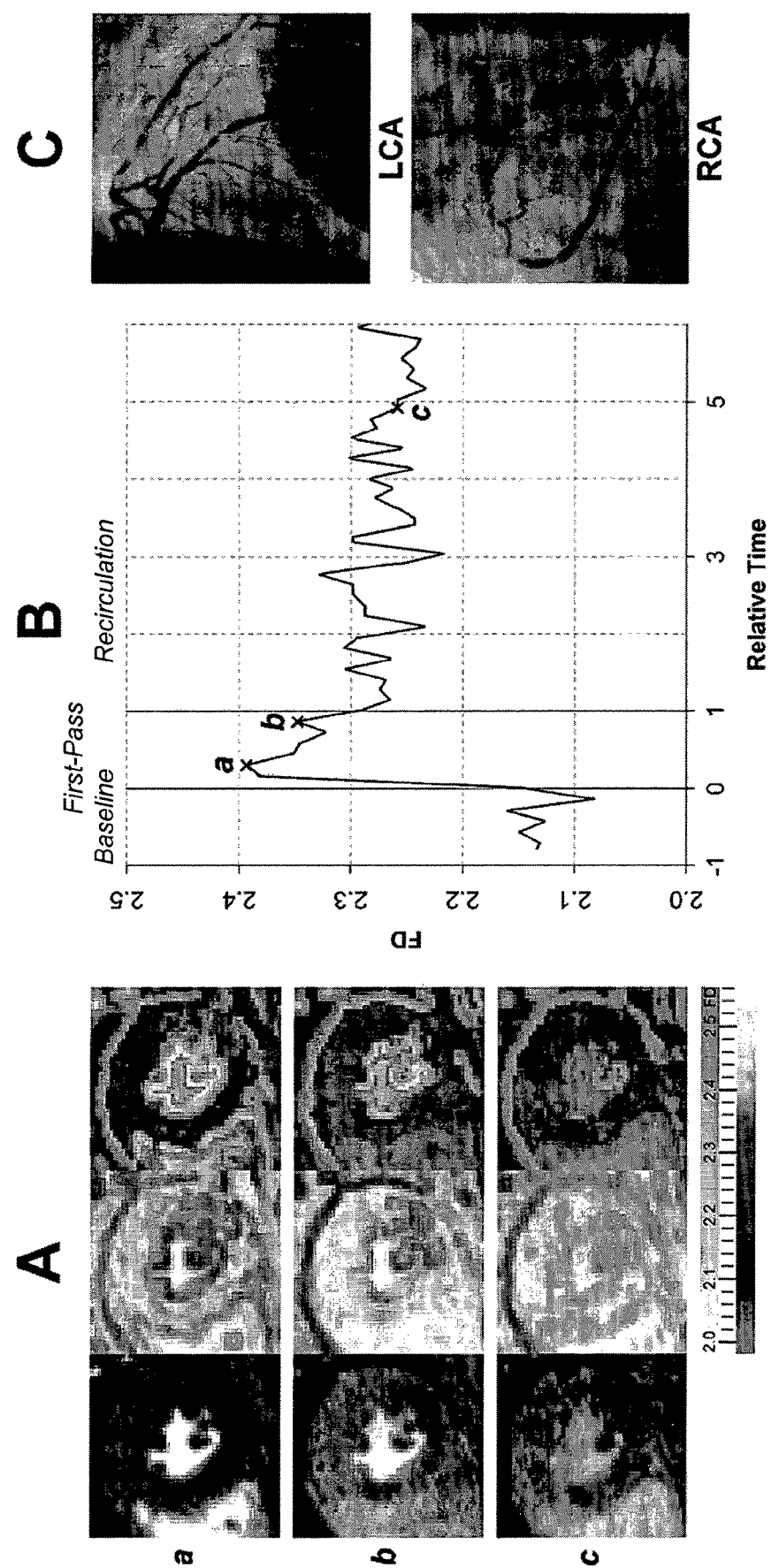
Figure 7:
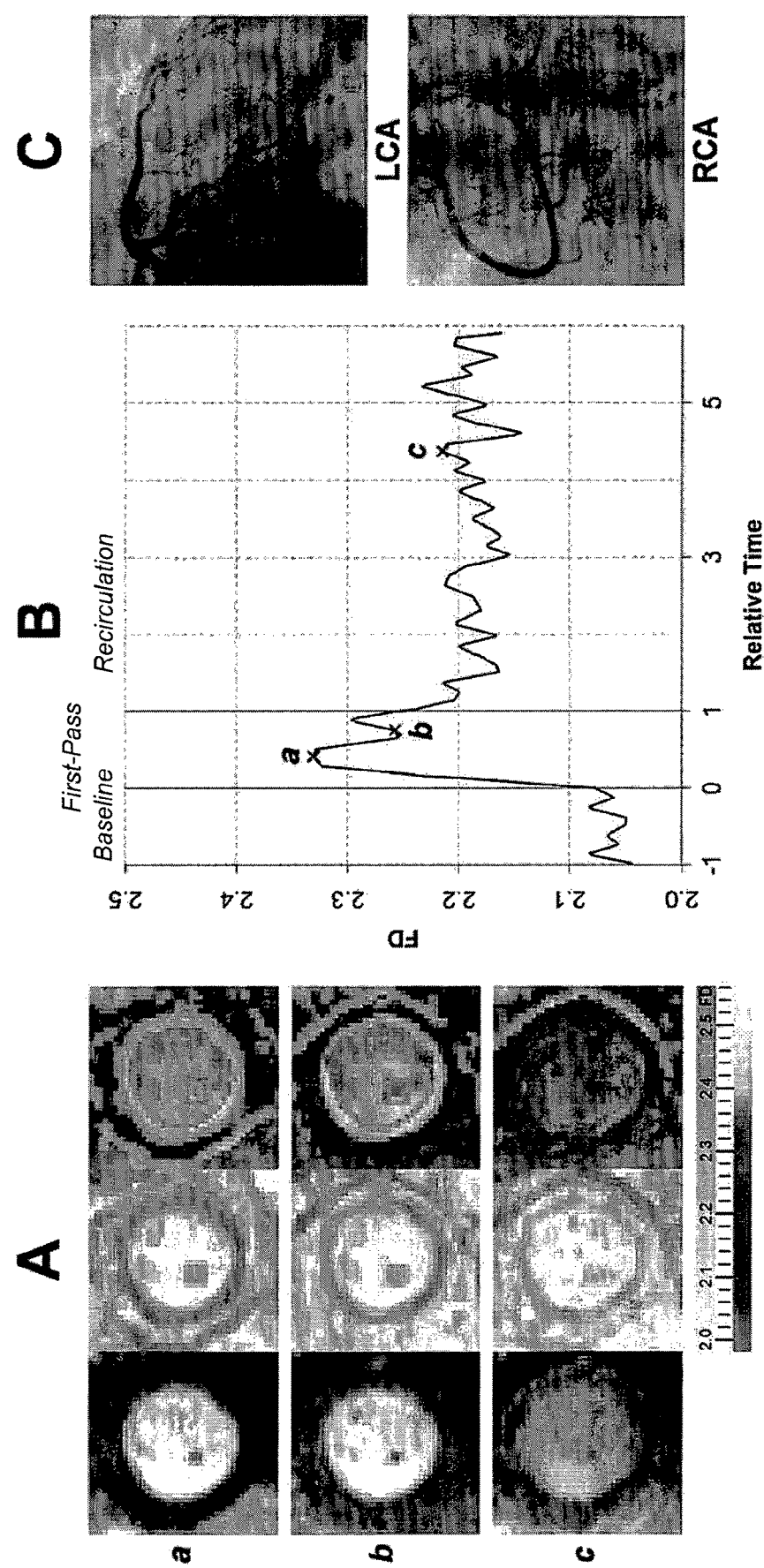

The method is further explained in more detail by means of the following examples with reference to the Figures. It shows:

FIG. 1 an overview of an example of the methodology of fractal analysis;

FIG. 2 diagrams illustrating temporal fractal dimension curves;

FIG. 3 diagrams illustrating plots of percent diameter stenosis vs. fractal dimension in recirculation by presumed pathomechanism according to fractal analysis;

FIG. 4 box-plots of fractal dimension in the different contrast medium kinetic phases by presumed pathomechanism according to fractal analysis;

FIG. 5 a scheme illustrating the fractal analysis of a normal control patient;

FIG. 6 a scheme illustrating the fractal analysis of a patient with a CAD lesion; and FIG. 7 a scheme illustrating the fractal analysis of a patient with a CMD lesion.

A specific embodiment of the present invention in order to prove its general feasibility and demonstrate exemplarily its capabilities is illustrated in the following by the example of fractal analysis of the ischemic interface region in chronic myocardial ischemia using MRI (Michallek and Dewey. Eur Radiol. 2016; DOI 10.1007/s00330-016-4492-2).

Pathophysioloqical Mechanisms of Chronic Myocardial Ischemia

In general, perfusion traverses the myocardium from the subepicardial towards the subendocardial layers, resulting in a perfusion front. This front comes to a halt at the site of an ischemic defect, i.e., where the compensatory vasodilator reserve fails to maintain perfusion. Because it is localized at the "vascular entrance", obstructive coronary artery disease (CAD) a priori restricts epicardial driving pressure to the subsequent vascular territory with the compensatory vasodilator reserve being increasingly challenged in centripetal direction of transmurality (Epstein S E, Cannon R O, 3rd, Talbot T L. Hemodynamic principles in the control of coronary blood flow. Am J Cardiol. 1985; 56: 4E-10E). Therefore, the subendocardial layers are most susceptible to the development of ischemia. Without significant collateralization, alternative sources of perfusion are sparse and convective arterial blood supply, i.e. perfusion, is compromised in the ischemic region. Hence, myocardial deposition of contrast agent during its first-pass phase through the myocardium is intensely restricted and diffusion from the outmost layers of the defect is insufficient to bridge impaired perfusion. Consequently, in case of CAD the interface region pathologically exhibits the genuine complexity of the variously scaled compensatory mechanisms of perfusion.

Coronary microvascular dysfunction (CMD), in contrast, can occur at many sites of the vasculature and may feature manifold anatomical and functional insufficiencies with a loss of proper vasodilation or development of pathological vasoconstriction on different vascular scales (Cannon R O, 3rd, Watson R M, Rosing D R, Epstein S E. Angina caused by reduced vasodilator reserve of the small coronary arteries. J Am Coll Cardiol. 1983; 1:1359-1373). CMD is considered a pathological state diffusively and systemically affecting coronary circulation with the subendocardial myocardium, again, being most susceptible to develop ischemia. Affected and healthy microvessels are present side by side in a patchy distribution pattern (Herrmann J, Kaski J C, Lerman A. Coronary microvascular dysfunction in the clinical setting: from mystery to reality. Eur Heart J. 2012; 33:2771-2782b). Unlike CAD, vasodilatory compensation is therefore patchily impaired. Consequently, arterial convection is still present in neighboring unaffected vascular beds and can partly counterbalance diseased vascular beds due to effective diffusive distances through the cellular meshwork. The interface region partly takes up contrast agent during the first-pass phase through convection, yielding a smoother transition from adequately perfused to ischemic myocardium as compared to CAD. The pattern of perfusion compensation in the interface region is thus masked and its complexity is diminished.

A third entity is epicardial stenosis, i.e. CAD, bypassed with significant collaterals. In this case, perfusion can be provided via an alternative source, though with a time delay (Jerosch-Herold M, Hu X, Murthy N S, Seethamraju R T. Time delay for arrival of MR contrast agent in collateral-dependent myocardium. IEEE Trans Med Imaging. 2004; 23:88 1-890). Similar to CMD, the pattern of compensation in the interface region becomes masked and its complexity is diminished.

It is suggested that myocardial ischemia is caused by a pathomechanical composition of CAD, CMD and presence or absence of collateral perfusion. The contributions of these mechanisms may vary from patient to patient and may even differ locally from one vascular territory to the next in the same patient.

Implementation of Fractal Analysis

An analysis software ("FraktalWandler") implementing a suited embodiment of the present invention has been specifically developed in the Java programming language. The implementation is summarized in FIG. 1.

Each myocardial segment (according to the AHA 17-segment model: Cerqueira M D, Weissman N J, Dilsizian V, Jacobs A K, Kaul S, Laskey W K, Pennell D J, Rumberger J A, Ryan T, Verani M S. Standardized myocardial segmentation and nomenclature for tomographic imaging of the heart. A statement for healthcare professionals from the Cardiac Imaging Committee of the Council on Clinical Cardiology of the American Heart Association. Circulation. 2002; 105:539-542) is individually inspected for ischemia in the MR images obtained with adenosine stress, and the ischemic segments identified in this way are subsequently subjected to further processing. In case of normal perfusion of that segment, no further processing is performed, except for one normally appearing segment being analyzed in each patient with at least one ischemic lesion. Hereby, the localization of the said perfusion front, which may physiologically occur in myocardial perfusion, is interpreted as physiological perfusion abnormality, thus featuring said interface region. This is done to obtain a physiological reference in each patient with ischemia. All images of the respective imaging series are processed with the proposed algorithm separately for each ischemic segment.

According to the description of the present method, further processing is subdivided into a pre-processing step and the FA.

During pre-processing, irrelevant complexity is eliminated by a pipeline of delicately balanced and individualized edge—or intensity-sensitive denoising filters before individual intensity transition. Pre-processing thus delineates ischemic myocardium and demarcates it from other sources of complexity within adequately perfused myocardium, e.g. noise.

The imaging dataset is loaded into the analysis software ("FraktalWandler"). Image pre-processing starts with defining baseline myocardial intensity in the respective myocardial segment as the spatial average value obtained from an appropriate myocardial region of interest (ROI) placed in the segment before contrast arrival. This ROI is also used to determine the standard deviation (SD) of intensity, which is processed at a later time. Peak myocardial intensity during first-pass phase of the contrast agent through the myocardium is analogously obtained from the image during first-pass in which mean myocardial intensity in the ROI is highest. Subsequently, original intensities are stored into an array. In a second, temporary, array, intensities are linearly scaled for the whole image such that baseline intensity is defined as 0 and peak first-pass intensity is defined as 1 using the following equation: $I_{scaled} = I_{original} - I_{baseline})/(I_{peak} - I_{baseline})$. Afterwards, a median filter is applied to the original intensities in a 3×3 neighborhood on condition that the corresponding scaled intensities in that neighborhood are all below or equal to 0.3. This is a crucial prerequisite for further processing as it ensures adequate noise reduction for the low-level intensity range reflecting myocardium before contrast arrival, which is supposed to be homogeneous, i.e. lacking major complexity except for noise, in the employed MRI sequence.

Again on the original data, a bilateral Gaussian filter is applied for general denoising with a low to moderate value of SD in the spatial domain, i.e. $\sigma_{domain}=0.8$. The SD in the intensity range ($\sigma_{range}$) is determined from local noise in the respective myocardial segment as the SD of intensity in the already drawn baseline ROI ($\sigma_{base}$) mentioned above before median filtering. $\sigma_{range}$ is then obtained by $\sigma_{range} \approx 1.64\sigma_{base}$ in order to encompass the 90% limit. This ensures noise-level-adapted filtering of the whole image series. The resulting filtered images are standardized by scaling intensity as described above.

Finally, each pixel's processed value is increased by one and its reciprocal is taken yielding new pseudo-intensities that are thus standardized according to myocardial baseline mean intensity and first-pass peak intensity and follow an asymptotic decreasing relationship. On the one hand, this procedure augments discriminability for hypoperfused myocardium, thus unveiling complexity and facilitating FA. On the other hand, myocardium that is adequately perfused is assimilated as it is supposed to be of little relevance for this specific embodiment of the present method and therefore to contain little diagnostic information.

Subsequent local FA yields maps of local FD, which can be displayed both as gray-level and color-encoded images with the option of image fusion with the original MR images.

A local FA (Novianto S, Suzuki Y, Maeda J. Near optimum estimation of local fractal dimension for image segmentation. Pattern Recognit Lett. 2003; 24:365-374) based on the blanket method (Peleg S, Naor J, Hartley R, Avnir D. Multiple resolution texture analysis and classification. IEEE Trans Pattern Anal Mach Intell. 1984; 6:518-523) is employed. This algorithm interprets an image as a three-dimensional texture with intensity encoding the texture's height. The texture is covered by a blanket with a top and a bottom surface. In each iteration, the direct neighbors of each pixel in a 3×3 neighborhood are checked against each other. If a neighboring pixel has a higher or lower value, it is adopted, else the pixel's intensity is incremented or decremented by 1, respectively:

$$u_\varepsilon(i, j) = \max\{u_{\varepsilon-1}(i, j) + 1, \max_{|(m,n)-(i,j)|\leq 1} u_{\varepsilon-1}(m, n)\}$$

$$b_\varepsilon(i, j) = \min\{b_{\varepsilon-1}(i, j) - 1, \min_{|(m,n)-(i,j)|\leq 1} b_{\varepsilon-1}(m, n)\}$$

$u_\varepsilon$ and $b_\varepsilon$, are the top and bottom surfaces, $\varepsilon$ is the counter of iterations, i, j, m and n are pixel coordinates. In each iteration step, the area A of the blanket is determined by the formula:

$$A(\varepsilon) = \frac{\sum_{i,j}(u_\varepsilon(i, j) - b_\varepsilon(i, j))}{2\varepsilon}$$

Novianto et al. have identified 44 as the optimal number of iterations. For a fractal texture, a plot of log $A(\varepsilon)$ against log $\varepsilon$ yields a decreasing straight line, i.e. the slope is negative. The FD of the texture is finally obtained by a linear fit of log $A(\varepsilon)$ against log $\varepsilon$:

$$FD=2-\text{slope}$$

The global FD for the texture or parts thereof can be obtained by averaging the respective local FDs.

Finally, FA is evaluated as follows. The temporal perfusion imaging series is divided into three perfusion phases according to contrast agent dynamics in the myocardium: a baseline phase including initial images without myocardial contrast enhancement; a subsequent first-pass phase, beginning with the image of first perceivable myocardial contrast uptake and ending with the image obtained after most of the contrast agent has passed the left ventricle; and a recirculation phase comprising subsequent images of a steady state of contrast. From these phases, arithmetic mean values ($FD_{baseline}$, $FD_{recirculation}$) and the maximum value ($FD_{first-pass}$) of FD were obtained.

An irregularly shaped ROI is placed within said interface region between the ischemic lesion and the adjacent, adequately perfused myocardium in that segment. For analysis of pre-contrast baseline images, the ROI is placed within the uncontrasted myocardium. If a perfusion defect has replenished during the recirculation phases, the ROI is placed at the site corresponding to the former interface region. After defining a ROI in each image of the series, the global FD is calculated at each point in time and changes over time are plotted by the software.

In this specific embodiment of the present method, $FD_{first-pass}$ is assumed to convey information about the pathomechanical composition. A threshold for classification remains to be determined; therefore, the 40-percentile and 60-percentile of $FD_{first-pass}$ from all ischemic segments were calculated and all ischemic segments with an $FD_{first-pass}$ above or equal to the 60-percentile were assigned to the presumed CAD group, and all ischemic segments with an $FD_{first-pass}$ below or equal to the 40-percentile were assigned to the presumed CMD or collateralization group. An additionally analyzed remote segment in each patient was assigned to the normal control group. FD values from the three phases were separately averaged according to group assignment and reported as mean±sample standard deviation (SD).

$FD_{recirculation}$ is supposed to be related to severity of ischemia. Therefore $FD_{recirculation}$ of each ischemic segment was plotted against the corresponding maximum percent diameter stenosis in ICA as a surrogate parameter for severity of CAD. It was expected that this would reveal some relationship between degree of stenosis (in invasive coronary angiography) and severity of ischemia for CAD (epicardial stenosis) but not for CMD (since the latter is independent of epicardial stenosis). Currently, no clinically available gold standard exists to confirm CMD. No further analysis was thus performed in this regard.

Furthermore, the temporal FD curve of each segment was plotted according to the assigned group using a centered moving average. For comparison, these curves were temporally standardized: the beginning and end points in time of first-pass in the MRI series were defined as $t_{rel}=0$ or $t_{rel}=1$, respectively, and time was linearly scaled, yielding a relative time axis. This was done to account for individual circulation times and to enable visual comparison of the curves. Moreover, the curves assigned to the same group were temporally averaged to obtain a representative curve for each of the three groups. R was used for statistical analysis and graph creation.

Patients

Data from a single center (Charité) of the CORE-320 study (Vavere A L, Simon G G, George R T, et al. Diagnostic performance of combined noninvasive coronary angiography and myocardial perfusion imaging using 320 row detector computed tomography: design and implementation of the CORE320 multicenter, multinational diagnostic study. J Cardiovasc Comput Tomogr. 2011; 5:370-381) and its MRI perfusion sub-study were analyzed. The study was approved by the institutional review board and the German Federal Office for Radiation Protection. Written informed consent was obtained from each patient. Eligibility criteria included patient age of 45-85 years, suspected or known CAD and clinical referral for invasive coronary angiography (ICA). Patients were excluded if they had contraindications to gadolinium-containing or iodinated contrast media used in ICA, including known allergy to these contrast agents, known kidney dysfunction, elevated serum creatinine (>1.5 mg/dL) or calculated creatinine clearance of <60 mL/min or known thyroid hyperfunction. Other exclusion criteria were contraindications to adenosine or beta-blockers, including allergy to these drugs, severe chronic obstructive lung disease, atrio-ventricular block of second or third degree, sick sinus syndrome, atrial fibrillation, bradycardia, prolongation of QT interval, systolic blood pressure <90 mmHg, pre-existing severe hypotension, decompensated cardiac insufficiency, unstable angina pectoris, therapy with dipyridamol, recent intake of methylxanthines or hypovolemia. Further exclusion criteria were a history of uncontrolled tachyarrhythmia, previous cardiac surgery, coronary intervention within the past 6 months, evidence of acute coronary syndrome with TIMI risk score >5 or elevated cardiac enzymes in the past 72 h or thrombolysis, known or suspected moderate or severe aortic stenosis, presence of intracardiac devices or metallic implants, high radiation exposure (≥5.0 rems) in the 18 months before consent, pregnancy, body mass index >40 kg/m$^2$ and inability to hold the breath for at least 15 s.

Cardiac Perfusion Imaging Using MRI

A 1.5-T scanner (MR Avanto, Siemens Healthcare, Erlangen, Germany) was used for MR imaging, which included a fast low-angle shot sequence (TurboFLASH) for acquisition of temporally resolved myocardial perfusion images (imaging parameters: TR 197.7 ms, TE 1.08 ms, TI 120 ms, flip angle 12°, image matrix 192×144 pixels). Three cardiac short axis views (basal, mid-ventricular, apical) and one view in the long axis were obtained during each heartbeat in a total of 60 heartbeats with intravenous administration of contrast agent (twice Dotarem, Guerbet, Villepinte, France, 0.1 mmol Gd/kg bodyweight, flow 4-6 ml/s). Images were first acquired after intravenous adenosine infusion (140 µg/kg bodyweight/min, for 4.5 minutes, Adenosin Life Medical, Carinopharm GmbH, Gronau/Leine, Germany) as pharmacological vasodilator stress and second without adenosine to capture the resting condition. Late-enhancement images were obtained after administration of the total dose of 0.2 mmol Gd/kg for perfusion imaging using an inversion-recovery fast low-angle shot sequence. In this specific study, FA was only performed in vasodilator stress MR images.

Reference Standard

Coronary angiograms were acquired using invasive coronary angiography (ICA) in all patients eligible for this study. Percent diameter stenosis in epicardial arteries as seen on ICA were obtained and served as the reference standard for interpretation of FA results. Each ischemic region was assigned to its assumed feeding vessel according to the AHA model of coronary anatomy and myocardial perfusion territories. Subsequently, the lesion with the largest percent diameter stenosis in the assumed feeding vessel, as seen on the angiogram, was extracted for statistical analysis.

Results

Fifty patients who met the inclusion criteria underwent MRI. Twenty-six of these patients had detectable myocardial ischemia (21 male, 5 female) and were therefore eligible for FA. A total of 109 ischemic segments during stress were identified and FA was successfully accomplished in 108 segments (21 in female patients). One segment was excluded due to thinned myocardium lacking adjacent normal myocardium uncontaminated by extramyocardial structures.

The procedure took 10 minutes per segment on average including pre-processing, FD map computation, evaluation of FA in individually drawn ROIs in each image and derivation of FD-versus-time curves. The 40- and 60-percentiles of $FD_{first-pass}$ were 2.335 and 2.387, respectively, with the corresponding classification assigning 43 lesions to presumed CAD (2 in female patients), 43 lesions to presumed CMD or collateralization (11 in female patients) and leaving 22 lesions unclassified (8 in female patients). Prevalence of segments with presumed CAD was 9.5% (2 of 21) in women and 47.1% (41 of 87) in men and with presumed CMD or collateralization 52.4% (11 of 21) in women and 36.8% (32 of 87) in men. Unclassified segments were present in 38.1% (8 of 21) of women and 16.1% (14 of 87) of men.

There were 18 patients with a homogenous pathomechanism classification, and 8 patients had lesions from both pathological groups. Fourteen ischemic segments in 5 patients (1 female) had no luminal reduction in the corresponding epicardial artery. Of these 14 lesions, FA assigned 10 to the presumed CMD or collateralization group (including the female patient, FIG. 3B), 3 to the presumed CAD group (all in one patient, FIG. 3A), and 1 was unclassified.

The FD-versus-time curves by group are displayed in FIG. 2. Time is linearly scaled on the basis of the beginning ($t_{rel}$=0) and end ($t_{rel}$=1) of first-pass as described in the Methods section. For conciseness, the presumed CMD or collateralization group is abbreviated as "presumed CM D".

FIG. 3 shows a plot of $FD_{recirculation}$ against the maximum corresponding percent diameter stenosis in ICA separately according to the presumed pathomechanism. Panel A depicts presumed CAD lesions as assigned by FA, Panel B depicts presumed CMD or collateralized lesions.

A box-plot of FD in the different perfusion phases by group is presented in FIG. 4.

FIG. 5 illustrates a normal control subject. A 69-year-old female patient without evidence of myocardial ischemia and no appreciable epicardial stenosis is depicted. Fractal analysis (FA) is performed in the antero-lateral segment of the mid-ventricular myocardial third (AHA segment 12). Panel A shows FA at three distinct points in time (a,b: during first-pass of the contrast agent, c: during recirculation). From left to right these are: the original MRI image, a gray-scale map of the local fractal dimension (FD) with the red area indicating the interface region of interest (ROI) of ischemic and adequately perfused myocardium, and a color-coded map of the local FD with the color scale given below. Note the physiological perfusion front with early enhancement of the subepicardial layers and a delay in the subendocardial layers (apparent during the initial first-pass, row a). Panel B depicts the resulting temporal FD curve of the ROI using the specified temporal standardization according to the duration of the first-pass. Baseline, first-pass and recirculation phases are indicated. The points in time depicted in panel A are marked (a, b, c). In panel C, coronary angiograms of the left and right coronary arteries (LCA, RCA) are displayed without evidence of epicardial stenosis. Compared to a low $FD_{baseline}=2.054$, FA reveals an initial peak of $FD_{first-pass}=2.199$, which corresponds to the physiological perfusion front and is followed by a quick decrease in FD. During recirculation, comparatively low complexity with a $FD_{recirculation}=2.057$ is observed. In conclusion, these findings indicate adequately perfused myocardium. As this patient had no evidence of ischemia, she was not included in the statistical analysis.

FIG. 6 discusses a CAD lesion matched with the coronary angiogram. A 54-year-old male patient with a 99% diameter stenosis in the right coronary artery (RCA, epicardial segment 1) and a matching ischemic defect is depicted. Fractal analysis (FA) is performed in the inferior segment of the mid-ventricular myocardial third (AHA segment 10). The panels are arranged analogously to FIG. 5. After an $FD_{baseline}=2.134$, FA reveals a high $FD_{first-pass}=2.393$, resulting in assignment of the lesion to presumed CAD. $FD_{recirculation}$ is elevated to an average of 2.262—a value presumably indicating relatively severe ischemia. In summary, these FA findings are consistent with the sub-occlusive RCA stenosis on angiography that matches the marked and persisting perfusion defect. Thus, FA correctly assigned the lesion to CAD as the predominant pathomechanism. Note the sub-occlusion in the left anterior descending artery (LAD) in segment 7 and a second ischemic defect in the anterior-septal segment (AHA segment 8), which however requires a segment-dedicated FA for proper appraisal.

FIG. 7 depicts an example of a CMD lesion. A 70-year-old male patient without epicardial coronary stenosis but ischemia of the inferior wall is depicted. Fractal analysis (FA) is performed in the infero-lateral segment of the basal myocardial third (AHA segment 5). The panels are arranged analogously to FIG. 5. FA shows an $FD_{baseline}=2.066$ and reveals an intermediate $FD_{first-pass}=2.331$, indicating a presumed CMD lesion. $FD_{recirculation}$ averages 2.187, consistent with moderate ischemia. In this patient with a normal coronary angiogram, MRI demonstrates a subendocardial perfusion defect which most likely originates from CMD and is correctly classified by FA.

The invention claimed is:

1. A method for characterizing perfusion abnormalities in tissue by means of fractal analysis (FA) of at least one part of an interface region between adequately and abnormally perfused tissue from an object of study that features perfusion wherein the interface region is defined as a region where adequately and abnormally perfused areas merge into each other, the method comprising the steps of:
    (A) identifying the at least one part of the interface region;
    (B) providing an imaging dataset of perfusion imaging; wherein said imaging dataset visualizes the at least one part of the interface region identified in step (A);
    (C) applying fractal analysis to the interface region visualized in the imaging dataset provided in step (B); wherein said fractal analysis provides at least one fractal parameter of the at least one part of the interface region.

2. The method according to claim 1, wherein the at least one fractal parameter comprises the fractal dimension (FD); and wherein the imagine dataset provided in step (B) is pre-processed after step (B) and before step (C).

3. The method according to claim 1, wherein the perfusion imaging is performed using an imaging modality or method capable of recording perfusion characteristics of tissue.

4. The method according to claim 1, wherein the perfusion imaging data are organized in a way that is accessible to data processing.

5. The method according to claim 1, wherein the at least one part of the interface region is analyzed by fractal analysis.

6. The method according to claim 1, wherein fractal analysis is performed at n (n≥1) individual phases of perfusion or a combination thereof.

7. The method according to claim 6, wherein the n (n≥1) individual perfusion phases are defined according to meaningful physical or physiological criteria.

8. The method according to claim 6, wherein at least one perfusion phase is defined.

9. The method according to claim 6, wherein fractal analysis is performed for at least one of the different perfusion phases.

10. The method according to claim 6, wherein at least two perfusion phases are defined.

11. The method according to claim 6, wherein at least three perfusion phases are defined.

12. The method according to claim 6, wherein fractal analysis is performed for at least two of the different perfusion phases.

13. The method according to claim 6, wherein fractal analysis is performed for at least three of the different perfusion phases.

14. The method according to claim 1, wherein the optional pre-processing of said imaging dataset comprises mathematical operations including noise filtering, intensity transitions, registration algorithms, segmentation algorithms or combinations, extensions or variations thereof.

15. A non-transitory computer-readable storage medium that stores a data processing program comprising a set of computer readable instructions for processing imaging data by fractal analysis, which, when executed by the computer, carries out all steps of the method according to claim 1.

16. The method according to claim 1, wherein the perfusion imaging is performed using an imaging modality or method capable of recording perfusion characteristics of at least one part of the interface region.

17. The method according to claim 1, wherein the perfusion imaging data are organized as an imaging dataset that comprises at least one temporally resolved image series consisting of i (i≥1) successively acquired individual images.

* * * * *

UNITED STATES PATENT AND TRADEMARK OFFICE
CERTIFICATE OF CORRECTION

PATENT NO. : 10,991,109 B2
APPLICATION NO. : 15/759586
DATED : April 27, 2021
INVENTOR(S) : Florian Michallek et al.

It is certified that error appears in the above-identified patent and that said Letters Patent is hereby corrected as shown below:

On the Title Page

Left column, item (71):
Please change "CHARITÉ—UNIVERSITÄTSMEDIZIN BERLIN, Berlin (DE)"
To correctly read:
--Florian MICHALLEK, Berlin (DE); Marc DEWEY, Berlin (DE)--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*